(12) United States Patent
Remsburg et al.

(10) Patent No.: US 8,226,663 B2
(45) Date of Patent: Jul. 24, 2012

(54) MICRODERMABRASION HAND PIECE PROVIDING AUTOMATIC LIMITATION OF SKIN HYPEREXTENSION

(76) Inventors: Irina Remsburg, San Diego, CA (US); Olexii Alex Yashchenko, San Diego, CA (US)

( * ) Notice: Subject to any disclaimer, the term of this patent is extended or adjusted under 35 U.S.C. 154(b) by 124 days.

(21) Appl. No.: 12/887,638

(22) Filed: Sep. 22, 2010

(65) Prior Publication Data
US 2011/0009882 A1   Jan. 13, 2011

(51) Int. Cl.
*A61B 17/50* (2006.01)
(52) U.S. Cl. ........................................................ 606/131
(58) Field of Classification Search .................. 606/131; 604/246–256, 118–121
See application file for complete search history.

(56) References Cited

U.S. PATENT DOCUMENTS

| | | |
|---|---|---|
| 6,423,078 B1 | 7/2002 | Bays |
| 6,592,595 B1 | 7/2003 | Mallett |
| 6,641,591 B1 | 11/2003 | Shadduck |
| 6,695,853 B2 | 2/2004 | Karasiuk |
| 6,926,681 B1 | 8/2005 | Ramey et al. |
| 7,678,120 B2 | 3/2010 | Shadduck |
| 7,789,886 B2 | 9/2010 | Shadduck |

*Primary Examiner* — Elizabeth Houston
(74) *Attorney, Agent, or Firm* — Timothy M. Barlow (57) ABSTRACT

A microdermabrasion hand piece includes an elongated body portion having a particle supply channel and a waste removal channel extending lengthwise, parallel to a longitudinal axis, through the body portion; a removable tip attachable to a proximal end of the body portion, the removable tip defining a treatment orifice; the particle supply channel being oriented to direct a stream of abrasive particles, which are drawn into and guided through the particle supply channel, substantially toward a center of the treatment orifice; and an automatic vacuum relief valve assembly oriented centrally in the hand piece and generally parallel to the longitudinal axis of the hand piece, the vacuum relief valve assembly being responsive to skin contact, wherein the hand piece provides automatic limitation on skin extension, wherein extension of the skin in the treatment orifice, beyond a predetermined limit, is prevented and excessive extension of skin of various thicknesses is eliminated.

15 Claims, 9 Drawing Sheets

MICRODERMABRASION HAND PIECE PROVIDING AUTOMATIC LIMITATION OF SKIN HYPEREXTENSION

CROSS REFERENCE TO RELATED APPLICATIONS

Not Applicable

FEDERALLY SPONSORED RESEARCH

Not Applicable

SEQUENCE LISTING OR PROGRAM

Not Applicable

FIELD OF THE INVENTION

The present invention relates to devices for dermatology and more particularly to a hand-held instrument with a proximal end that carries (i) a negative pressure aspiration system, (ii) a source for delivery of a liquid or gas-laden abrasive mixture to the epidermis; and (iii) a skin interface surface in the proximal end that prevents hyperextension of the skin when connected to a vacuum relief valve in the distal end of the hand piece.

BACKGROUND

Dermatologists and plastic surgeons have used various methods for removing superficial skin layers to cause the growth of new skin layers (i.e., commonly described as skin resurfacing techniques) since the early 1900's. Early skin resurfacing treatments used an acid such as phenol to etch away surface layers of a patient's skin that contained damage to thereafter be replaced by new skin. (The term damage when referring to a skin disorder is herein defined as any cutaneous defect, e.g., including but not limited to rhytides, hyperpigmentation, acne scars, solar elastosis, other dyschromias, stria distensae, seborrheic dermatitis).

Following the removal of surface skin layers at a particular depth, no matter the method of skin removal, the body's natural wound-healing response begins to regenerate the epidermis and underlying wounded skin layers. The new skin layer will then cytologically and architecturally resemble younger and more normal skin. The range of resurfacing treatments can be divided generally into three categories based on the depth of the skin removal and wound: (i) superficial exfoliations or peels extending into the epidermis, (ii) medium-depth resurfacing treatments extending into the papillary dermis, and (iii) deep resurfacing treatments that remove tissue to the depth of the reticular dermis.

Microdermabrasion uses an air-pressure source to deliver abrasive particles directly against a patient's skin at high-velocities to abrade away skin layers. Microdermabrasion as currently practiced falls into the category of a superficial resurfacing treatment.

It is useful to briefly explain the body's mechanism of actually resurfacing skin in response to the removal of a significant depth of dermal layers. Each of the above-listed depths of treatment disrupts the epidermal barrier, or a deeper dermal barrier (papillary or reticular), which initiates varied levels of the body's wound-healing response. A superficial skin layer removal typically causes a limited wound-healing response, including a transient inflammatory response and limited collagen synthesis within the dermis. In a medium-depth or a deep treatment, the initial inflammatory stage leads to hemostasis through an activated coagulation cascade. Chemotactic factors and fibrin lysis products cause neutrophils and monocytes to appear at the site of the wound. The neutrophils sterilize the wound site and the monocytes convert to macrophages and elaborate growth factors which initiate the next phase of the body's wound-healing response involving granular tissue formation. In this phase, fibroblasts generate a new extracellular matrix, particularly in the papillary and reticuilar dermis, which is sustained by angiogenesis and protected anteriorly by the reforming epithelial layer. The new extracellular matrix is largely composed of collagen fibers (particularly Types I and III) which are laid down in compact parallel arrays. It is largely the collagen fibers that provide the structural integrity of the new skin—and contribute to the appearance of youthful skin.

All of the prevalent types of skin damage (rhytides, solar elastosis effects, hyperpigmentation, acne scars, dyschromias, melasma, stria distensae) manifest common histologic and ultrastructural characteristics, which in particular include disorganized and thinner collagen aggregates, abnormalities in elastic fibers, and abnormal fibroblasts, melanocytes and keratinocytes that disrupt the normal architecture of the dermal layers. It is well recognized that there will be a clinical improvement in the condition and appearance of a patient's skin when a more normal architecture is regenerated by the body's wound-healing response. Of most significance to a clinical improvement in skin is the creation of more dense parallel collagen aggregates with decreased periodicity (spacing between fibrils). The body's wound-healing reaction is responsible for synthesis of these collagen aggregates.

The superficial treatment offered by microdermabrasion has the advantages of being performed without anesthetics and requiring no extended post-treatment recovery period. However, microdermabrasion as currently practiced also has a large disadvantage. Current microdermabrasion devices cause abrasive effects in a focused area of the skin that is very small, for example roughly 20 $mm^2$ to 200 $mm^2$, since all current devices use a single-hole orifice that jets air and abrasives to strike the skin in a highly focused area. Such a focused treatment area is suitable mainly for superficial exfoliations when the proximal end of the device is passed over the skin in overlapping paths.

An important part of creating the skin healing response is the mechanical stretching of the skin caused by the vacuum hand piece. However, different regions of skin have different thickness and elasticity. For example, the eyelids are roughly 0.3 mm thick, while the skin on the back is roughly 3.0 mm thick. Obviously, applying the same vacuum level to various regions of the skin may cause a range of effects, including no effect, acute trauma or somewhere in between. The vacuum level is set by the operator, and the amount of vacuum is established, based in great part, due to the experience of the operator. Even with an experienced operator, working on a specific region of the body, for example face and neck, the vacuum level must be continuously adjusted to maintain the balance between too little mechanical stretching (with no benefit) and too much mechanical stretching (causing trauma).

REFERENCES

Freedman, Bruce, Eugenia Rueda-Pedraza, M D, and Sharon Waddell. "The Epidermal and Dermal Changes Associated with Microdermabrasion." Dermatologic Surgery 27 (2001):1031-1034.

Rajan, Poonam, and Pearl Grimes M D. "Skin Barrier Changes Induced by Aluminum Oxide and Sodium Chloride Microdermabrasion." Dermatologic Surgery 28 (2002):390-393.

Karimipour, Darius, et al. "Microdermabrasion: A molecular analysis following a single treatment." Journal of the American Academy of Dermatology 52.2 (2005):215-23.

Hernandez-Perez, Enrique, and Erick Valencia Ibiett, M D. "Gross and Microscopic Findings in Patients Undergoing Microdermabrasion for Facial Rejuvenation." Dermatologic Surgery 27 (2001):637-40.

Darius J. Karimipour, et al. "Molecular Analysis of Aggressive Microdermabrasion in Photoaged Skin." *Arch Dermatol.* 145-10 (2009):1114-1122

DESCRIPTION OF PRIOR ART

U.S. Pat. No. 6,592,595 to Mallett on Jul. 15, 2003 for "Microdermabrasion and suction massage apparatus and method" includes the combination of a microdermabrasion and suction massage apparatus in a single unit. The microdermabrasion section of the unit includes a crystal pickup station that draws crystals through a hole into an air stream. The step is followed by performing a suction massage procedure at the operative site in order to promote the healing of the abraded skin. A first air stream is directed through a source of crystals which are introduced into the first air stream to provide a flow of crystals which is then sent to the microdermabrasion hand piece. This discloses the concept of the microdermabrasion machine having crystals sprayed onto the skin.

U.S. Pat. No. 6,423,078 issued to Bays on Jul. 23, 2002 for "Dermabrasion Instrument, Instrument Assembly And Method" is a dermabrasion instrument which includes an outer member which is held stationary by a handpick and an inner member which is disposed at least partly within the outer member and rotated by the hand piece.

U.S. Pat. No. 6,926,681 issued to Ramey et. al. on Aug. 9, 2005 for "Method and System for Performing Microabrasion and Suction Massage" discloses a method and system for performing microdermabrasion. This is another patent application which discloses a variation on the concept of spraying abrading crystals onto the skin through a microdermabrasion machine.

U.S. Pat. No. 6,695,853 issued to Karasiuk on Feb. 24, 2004 for "Microdermabrasion System and Method of Use" discloses an applicator tool with a non-abrasive tip with one opening therethrough and an abrasive member located internally of the applicator tool and means for applying a vacuum so that a portion of the skin is drawn into contact with the abrasive member and abraded.

U.S. Pat. No. 6,641,591 issued to Shadduck on Nov. 4, 2003 for "Instruments and Techniques for Controlled Removal of Epidermal Layers" discloses an instrument for controlled removal of epidermal layers. In this case the patent discloses a handheld instrument having a vacuum aspiration system, a source to deliver sterile fluids or pharmacological agents onto the skin, and a skin interface surface in the end that has a special shape for abrading the layers of the skin as the end is moved over the patient's skin while at the same time causing rapid penetration of the fluids into the skin.

U.S. Pat. No. 6,641,591 granted on Nov. 4, 2003, U.S. Pat. No. 7,678,120 granted on Mar. 16, 2010, and U.S. Pat. No. 7,789,886 granted on Sep. 7, 2010, all to Shadduck, and all entitled "Instruments and Techniques for Controlled Removal of Epidermal Layers" disclose the use of a bleed valve (vacuum relief valve) located in the vacuum line between the vacuum generator and the hand piece.

SUMMARY OF THE INVENTION

The present invention seeks to improve upon the field of microdermabrasion machines with an improved hand piece wherein a proximity-sensing vacuum relief valve prevents excessive vacuum from causing an adverse reaction to a microdermabrasion procedure.

A microdermabrasion hand piece includes an elongated body portion having a particle supply channel and a waste removal channel extending lengthwise, parallel to a longitudinal axis, through the body portion; a removable tip attachable to a proximal end of the body portion, the removable tip defining a treatment orifice; the particle supply channel being oriented to direct a stream of abrasive particles, which are drawn into and guided through the particle supply channel, substantially toward a center of the treatment orifice; and an automatic vacuum relief valve assembly, which is sensitive to skin contact, oriented centrally in the hand piece and generally parallel to the longitudinal axis of the hand piece, the vacuum relief valve assembly being responsive to skin contact, wherein the hand piece provides automatic limitation on skin extension, wherein extension of the skin in the treatment orifice beyond a predetermined limit is prevented and excessive extension of skin of various thicknesses is eliminated.

This arrangement provides advantages over the prior art, including that excessive skin extension is automatically eliminated for a wide range of skin thicknesses and types, which eliminates or greatly reduces the possibility of a reverse action, damage to the structure of the skin and damage to capillary blood flow.

In accordance with one aspect of the invention, the vacuum relief valve assembly includes an axially-movable skin probe which is oriented centrally in the hand piece and parallel to the longitudinal axis of the hand piece, the skin probe being movably attached to the distal end of the hand piece and movable in response to skin contact. This arrangement provides the advantage of a mechanism which is in a position to be highly responsive to skin extension.

In accordance with a further aspect of the invention, axial displacement of the movable skin probe opens a valve to admit ambient air and reduce the vacuum pressure inside the hand piece. This arrangement provides a rugged assembly which exhibits repeatable, reliable performance, which reduces the possibility of excessive skin extension and damage.

In accordance with another aspect of the invention, the vacuum relief valve assembly is user-adjustable for a maximum acceptable skin extension to be achieved before automatic actuation of the vacuum relief valve occurs. This arrangement provides the advantage of a device which can be fine-tuned for optimal performance in a wide variety of conditions, including the variability of ambient air pressure, vacuum pressure, individual hand piece variations, and skin variations between subjects.

According to a further aspect of the invention, an abrasive supply jet is radially displaced from the longitudinal axis of the hand piece, wherein the stream of abrasive particles exits the particle supply channel at a point which is radially displaced from the vacuum relief valve assembly on the longitudinal axis of the hand piece. This provides an advantage in that the radial displacement of the abrasive supply jet of the particle supply channel provides a centralized location for the proximity-sensing vacuum relief valve assembly within the treatment orifice.

According to another aspect of the invention, the particle supply channel is angularly offset relative to the longitudinal axis of the hand piece wherein delivery of the stream of abrasive particles is not parallel to the longitudinal axis. This arrangement provides an advantage in that the radially-displaced abrasive supply jet, to which the particle supply channel is attached, can deliver the abrasive supply into the desired portion of the treatment orifice.

In accordance with a further embodiment of the invention, the diameter of the waste removal channel inside the proximal end of the hand piece is larger than the diameter of the particle supply channel. This arrangement provides an advantage in that the vacuum source has a larger area of influence within the area of the treatment orifice, which improves the effectiveness of the waste removal system.

According to another embodiment of the invention, the diameter of the waste removal channel inside the proximal end of the hand piece is 1.5 to 3 times larger than the diameter of the particle supply channel.

In accordance with an additional embodiment of the invention, the treatment orifice is generally perpendicular to the longitudinal axis of the hand piece. This arrangement provides an advantage in that the handpiece is always oriented generally perpendicular to the surface of the skin being treated, which quick and easy to verify.

According to a further embodiment of the invention, the treatment orifice is angled with respect to the longitudinal axis of the hand piece. This arrangement provides the advantage in that the hand piece may be angled with respect to the skin surface, and held like a pencil for treatment.

According to another embodiment of the invention, the axially-movable skin probe includes one or more non-rotation tabs oriented longitudinally along the surface of the skin probe and projecting radially from the skin probe, said non-rotation tabs engaging one or more corresponding slots in a generally tubular main body, said main body being attached to the distal end of the hand piece body. This provides the advantage that any input received through the skin probe is converted to axial movement, and the probe cannot simply rotate on the longitudinal axis.

According to a further embodiment of the invention, the device further includes an adjustment thumbscrew having a manually-manipulated head and a threaded shaft extending longitudinally therefrom, the threaded shaft having male threading and extending through the generally tubular main body, wherein the male threading engages the female threading of the distal end of the axially-movable skin probe, wherein rotation of the adjustment thumbscrew adjusts the axial position of the skin probe with respect to the treatment orifice, and adjusts the sensitivity of the axially-movable skin probe to skin contact. This provides the advantage of almost infinite placement options, and sensitivity options, for the skin probe with respect to the treatment orifice.

According to another embodiment of the invention, the one or more slots in the generally tubular body are limited to the proximal end of the main body, such that the axially-movable skin probe cannot move axially entirely through the main body, and the hand piece further includes a coil spring between the adjustment thumbscrew and the main body, wherein the adjustment thumbscrew is biased away from the main body under spring pressure, and the axially-movable skin probe is drawn into the main body, wherein vacuum pressure within the hand piece overcomes the biasing force of the spring and draws the adjustment thumbscrew-skin probe assembly toward the proximal end of the hand piece, wherein rotation of the adjustment thumbscrew adjusts the sensitivity of the axially-movable skin probe to skin contact in a predictable manner. This provides an advantage in that the skin probe, though movable, is positively retained in the device. Further, the spring is quite weak, which, advantageously, means that the vacuum pressure can be kept very low, if necessary, and the device will still function properly.

According to a further embodiment of the invention, the hand piece further includes an elastomeric seal around the shaft of the adjustment thumbscrew immediately adjacent the manually-manipulated head, wherein the elastomeric seal bears against a corresponding sealing surface in the distal end of the main body to provide a positive and releasable vacuum seal, wherein axial movement of the skin probe, in response to skin contact, unseats the elastomeric seal and reduces the vacuum pressure within the hand piece and treatment orifice. This provides the advantage of a positive, repeatable and predictable relief valve, which is important to prevent skin damage.

According to another embodiment of the invention, the microdermabrasion hand piece further includes a rotation indicator on the manually-manipulated head of the adjustment thumbscrew, providing visual confirmation of a relative sensitivity of the hand piece.

According to the present invention, a novel apparatus and process is provided which alleviates the problems with prior art devices as stated above, and which provide other operational improvements as well.

A first aspect of the invention is the provision of a novel hand piece having several important features.

The proximity-sensing vacuum relief valve assembly is responsive to skin contact, skin contact being indicative of the degree of skin extension and distortion. This arrangement provides the advantage of using the detected skin extension and distortion to limit the application of vacuum and thereby limit the degree of skin extension, to reduce or eliminate hyperextension, and reduce or eliminate the risk of skin trauma.

The particle stream exits the particle supply channel at a point which is radially displaced from the longitudinal axis of the hand piece, but the particle supply channel may be oriented so that the stream of abrasive particles is directed substantially toward the center of the treatment orifice.

Other features of the invention, and advantages over the prior art will become apparent from consideration of the following detailed description in conjunction with the drawings.

DRAWING REFERENCE NUMERALS

10—view of prior art microdermabrasion device and method
11—proximal end of hand piece, relative to skin
12—orifice at proximal end of hand piece
13—hand piece body
14—subject's skin
15—vacuum space inside hand piece
16—supply conduit for abrasive particles
17—abrasion particle flow
18—hyperextension of skin
19—location of abrasion particle impact
20—cross section of typical skin
21—epidermis
22—dermis
23—epidermal collagen
24—papillary layer
25—reticular layer
26—hair
27—nerves
28—wrinkle
30—microdermabrasion system
31—vacuum generator
32—vacuum level adjustment
33—abrasive feed device
34—abrasive supply canister
35—subject
36—hand piece assembly
37—air filter
38—waste collection device
39—waste filter
40—flow meter
41—abrasive concentration controller
42—vacuum gauge
43—relief valve
45—abrasive particles
51—proximal end of hand piece
52—body of hand piece
53—distal end of hand piece
54—abrasive supply port
55—exhaust port
56—adjustment thumbscrew
57—operation orifice
58—abrasive supply jet
59—proximity sensing skin probe tip
60—proximity sensing vacuum relief valve assembly
61—skin probe shaft
62—non-rotation tabs
63—female adjustment threads
64—main body of relief valve
65—non-rotation slots
66—assembly slots
67—main body outer threads
68—compression spring
69—elastomeric seal
71—knurled surface
72—rotation indicator
73—male adjustment threads
74—hand piece cavity pressure
75—ambient pressure
76—sealing surface
77—exhaust conduit
78—entrance to exhaust conduit
81—normal skin extension
82—subject's skin
83—force caused by pressure imbalance
84—extension of subject's skin
85—upward motion

DETAILED DESCRIPTION OF THE DRAWINGS

Prior Art

Figure 1:
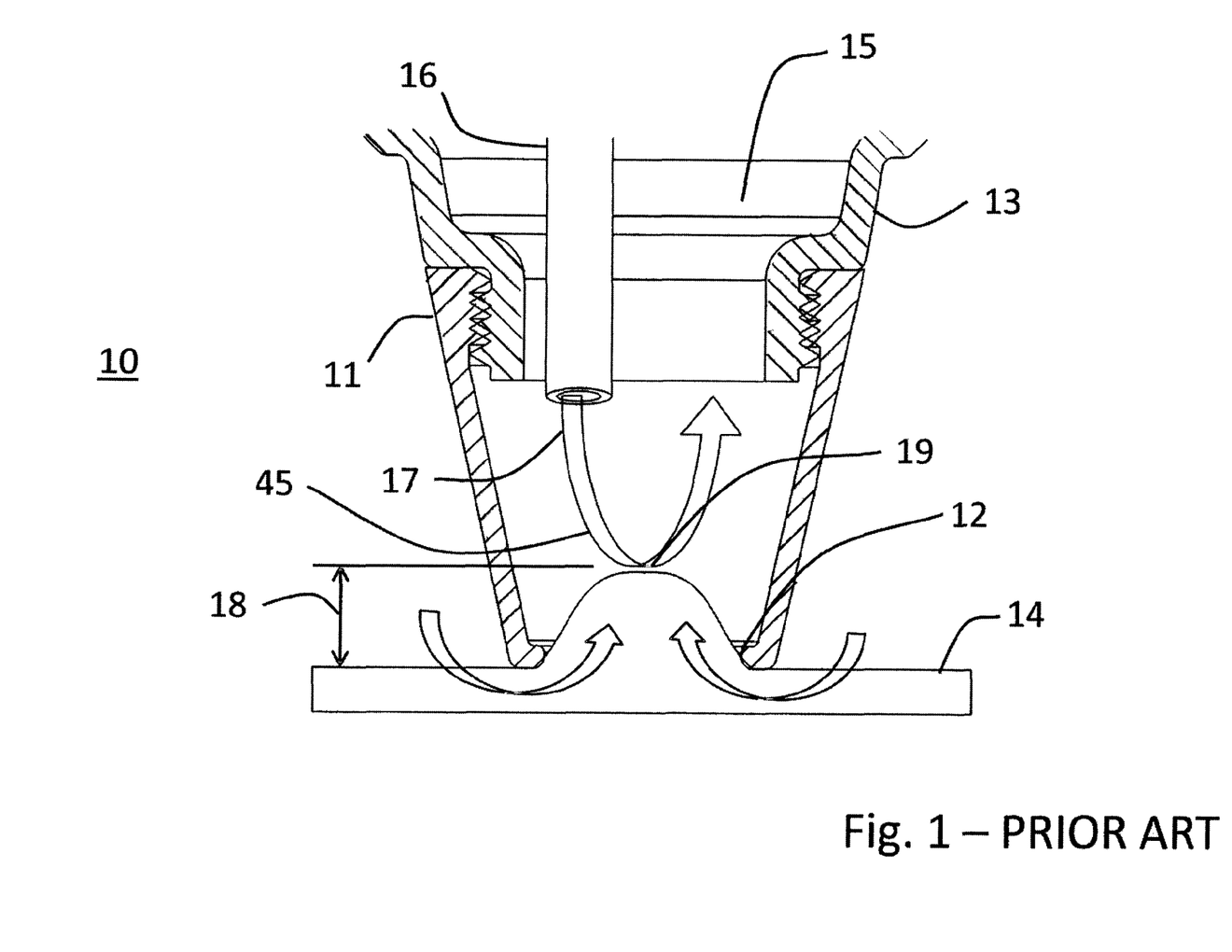
FIG. 1 illustrates a cross section view of the proximal end of a microdermabrasion hand piece, and the resulting hyperextension of the subject's skin, according to the prior art.
Figure 3:
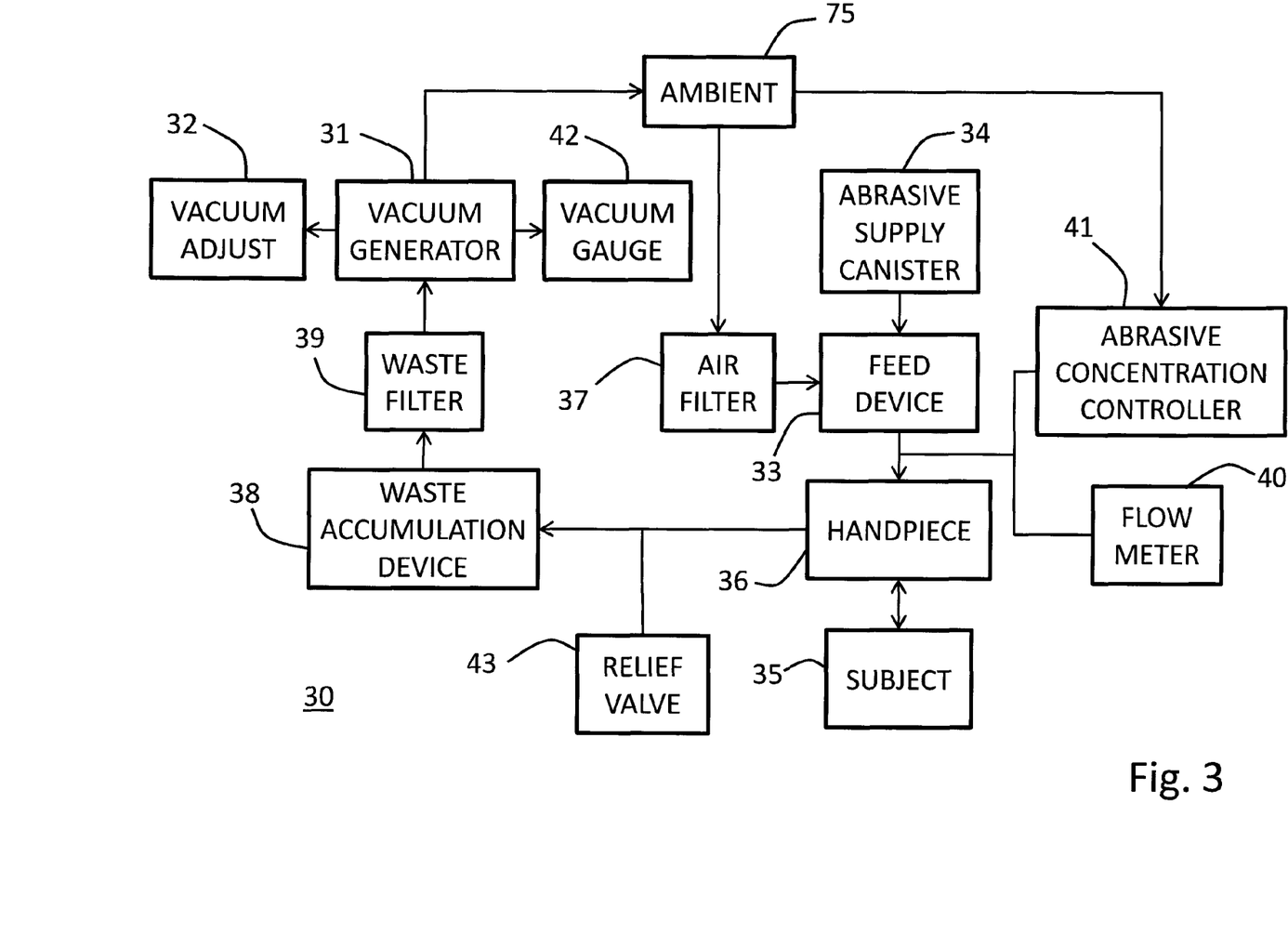
FIG. 3 is a block diagram showing the various components of a microdermabrasion system.

FIG. 1 illustrates a cross section view of the proximal end 11 of a microdermabrasion hand piece, according to the prior art, and the resulting hyperextension 18 of the subject's skin 10 which results from the use of the prior art device. A prior art hand piece 10 is composed of a proximal end 11 with an orifice 12, and a hand piece body 13. In operation, orifice 12 at the proximal end 11 of the hand piece 10 is against, and closed by, a subject's skin 14. Sealing of orifice 12 by the subject's skin 14 allows a vacuum to build in the interior space 15 of the hand piece 10. An abrasive supply conduit 16 is connected to a source of abrasion particles which may be maintained at ambient pressure. Vacuum within the interior space 15 of the hand piece 10 draws in and causes a flow of abrasion particles 17 through the hand piece 10. Vacuum within the hand piece 10 causes subject's skin 14 to be hyperextended 18 into the hand piece through orifice 12. Abrasion particles 45 impact the subject's skin 14 at location 19. Hyperextension 18, beyond a limit which varies based upon numerous factors, of the subject's skin 14 can cause skin trauma and may rupture capillaries, veins and arteries. Hyperextension 18 of the subject's skin 14 into the hand piece 10 also reduces the distance between the outlet of supply conduit 16 and the subject's skin 14 resulting in a more localized abrasion effect at location 19, which can exacerbate the detrimental internal effects of skin hyperextension. Referring to FIG. 3, a relief valve or bleed valve 43 is often added to the system 10 to control the vacuum level in interior space 15 of prior art devices, such as illustrated in FIG. 1.

Present Invention

Figure 2:
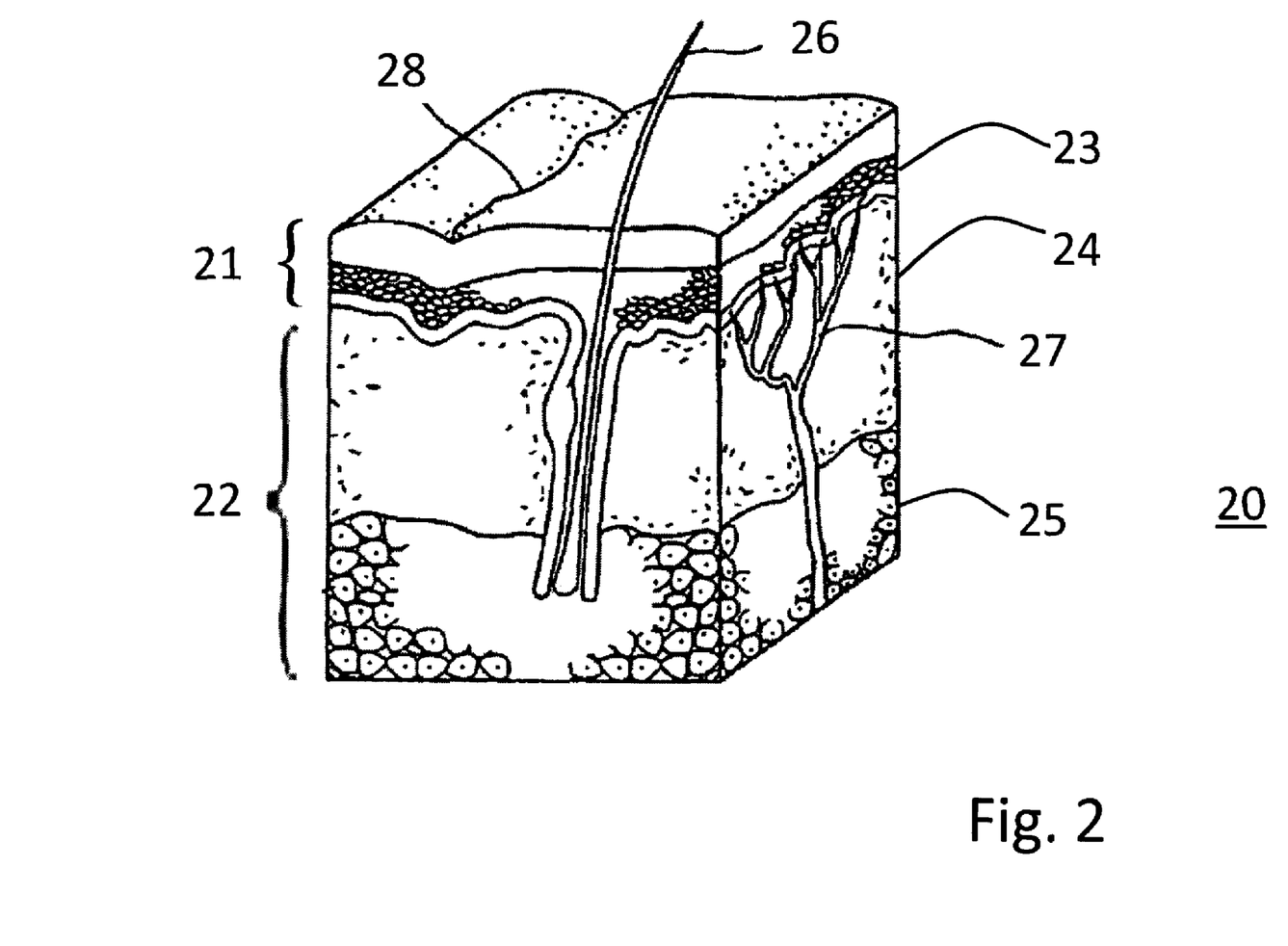
FIG. 2 illustrates an isometric cross section view of a subject's skin.

FIG. 2 illustrates a cross-section view of typical skin tissue 20. The uppermost layer of typical skin tissue is composed of dead cells. Underneath these dead skin cells is an outer layer, the epidermis 21 and a thicker inner layer, the dermis 22. Epidermis 21 contains a thin layer of collagen 23. Dermis 22 is composed of a papillary layer 24 and a reticular layer 25. Papillary layer 24 may contain diminished collagen aggregates. Reticular layer 25 of dermis 22 is made up of dense irregular connective tissue. Fibroblasts are found in dermis 22. Fibroblasts produce collagen. One of the goals of microdermabrasion is to increase the collagen content of epidermal collagen layer 23 and papillary layer 24. Intertwining S-like finger shaped portions of collagen are at the interface between epidermal papillary layer 24 and the dermal papillary layer. Dermis layer 22 contains the major part of the connective collagen. Other structures found in typical skin include hair 26, nerves 27 and a wrinkle 28. It will be understood that the drawing is representative of typical skin and that the collagen matrix will take different forms in different parts of the body. For example, in the face, the eyelids and cheeks have dermis and subcutaneous layers which are significantly thinner with less fat than in other areas.

FIG. 3 depicts a block diagram of a microdermabrasion system in accordance with the present invention. A microdermabrasion apparatus 30 is a pneumatically driven apparatus that includes a vacuum generator 31. The pneumatic source may also be provided by a forced air system well known to those skilled in the art. Other pneumatic delivery systems will be readily apparent to those skilled in the art and should not be limited to solely a vacuum generator system or other forced air or compressed air delivery type arrangements. An airless pump may also be substituted as long as it provides adequate abrasive delivery and pick up though out the abrasion system. Those well skilled in the art may change the pneumatic system to a liquid system for alternate benefits.

Vacuum generator 31 also may be optionally coupled or decoupled from the remaining elements of the microdermabrasion apparatus 30 and is not intended to be limited to only those microdermabrasion systems that include self-contained pneumatic delivery systems. Further, since microdermabrasion apparatus 30 can utilize vacuum generator 31 as disclosed in the cited patent applications, it is possible to have both a microdermabrasion apparatus and a massage or body contouring system.

Vacuum generator 31 couples to other elements within system 30 via standard connection means. Vacuum generator 31 also vents to ambient 75 during operation. A vacuum adjustment control 32 is provided with the generator to control the level of vacuum pressure generated thereby. The connection means can include metal or plastic tubing typically found in systems that are pneumatically operated. Vacuum generator 31 typically generates a vacuum level of roughly 200 millibar.

The system 30 further includes an abrasive feed device 33 that couples to an abrasive supply canister 34 as well as to ambient 75. Abrasive supply canister 34 contains abrasive particles 45 that are 1 µm to about 50 µm in maximum cross-sectional dimension, (for example, aluminum oxide crystals). Preferably, the crystals are from about 5 µm to about 30 µm in maximum cross-sectional dimension to allow a very fine abrasion of the epidermis. The ambient connection provides the needed air to deliver the abrasive from abrasive feed device 33 to the patient subject 35. An air filter 37 is placed between the ambient source and abrasive feed device 33 to filter the incoming air supply as well as to prevent any abrasive within device 33 from exiting out the intake port from which ambient air 75 is drawn. Air filter 37 can be a sintered plastic, ceramic, or metallic filter that allows air to pass through, but not the abrasive. Other filters that can be utilized will be apparent to those skilled in the art such as membrane, fiber, and mesh filters, but are not limited solely to those named.

Abrasive feed device 33 further couples to a hand piece 36 or wand, which is utilized to perform the microdermabrasion on a patient or subject 35. The hand piece 36 provides both delivery of the abrasive material 45 to the subject as well as retrieval of waste debris and abrasive during operation. This excess debris and material is deposited in waste collection device 38, which is also coupled to hand piece 36. A waste filter 39, such as another sintered or other suitable filter, serves to prevent any previously untrapped waste debris and abrasive from contaminating vacuum generator 31 or being vented to ambient 75, and is coupled between the waste collection canister 38 and vacuum generator 31. Waste collection or accumulation device 38 may include an additional filter that is used to prevent the vast majority of waste debris and abrasive from reaching waste filter 39 or vacuum generator 31.

Apparatus 30 includes a flow meter 40 and an abrasive concentration controller 41. Flow meter 40 displays the airflow generated within apparatus 30 so that the technician operating apparatus 30 can determine whether the airflow is sufficient for the procedure. Furthermore, flow meter 40 can also be used as a diagnostic device to determine if air flow within the system has fallen below acceptable levels due to clogging or fouling of filters. Should the technician need to adjust the airflow, the technician utilizes the vacuum level controller 32.

Additionally, it may be desirable to vary the amount of abrasive in the air stream depending upon the nature of the procedure being performed. Toward this end, the operator utilizes abrasive concentration controller 41 to mix ambient air 75 into the abrasive-laden air coming from feed device 33 and leading toward hand piece 36. Flow meter 40 is well known to those skilled in the art and may be placed anywhere within the system where clean air flow occurs, i.e. before feed device 33 or after waste filter 39. In this example, the flow meter 40 and concentration controller 41 are both located proximate the hand piece 36.

Abrasive concentration controller 41 can be selected from a variety of controllers. For example, controller 41 can be an infinitely adjustable rotary type that goes from fully open to fully closed. It is the level of openness that determines the abrasive concentration in the system. Fully open, which couples the hand piece 36 to ambient 75 and bleeds air into the system effectively reduces abrasive concentration to zero such that no abrasive is being delivered but that air flow and vacuum pressure remains unchanged. Such a situation is advantageous for removing used abrasive and debris from the patient's skin, as is often desired at the end of a treatment. Conversely, fully closed maximizes abrasive concentration. A multi-position toggle switch may also be utilized that selects between fully open, fully closed, or one or more levels in between.

Further still, both flow meter 40 and abrasive concentration controller 41 can be either manually adjustable or electrically or electronically adjustable, depending upon the types of gauge sensor and pressure adjustment means selected and implemented. Electronic control provides for greater precision in abrasive delivery and treatment consistency between treatment sessions.

A vacuum gauge 42 and vacuum pressure adjustment means 32 are found on vacuum generator 31 within apparatus 30. Vacuum gauge 42 and adjustment means 32 are well known in the art.

A vacuum relief valve 43 is typically connected within the system to limit the amount of negative pressure which can be brought upon the skin. Relief valve 43 is typically disposed downstream of hand piece 36, between hand piece 36 and vacuum source 31. Those skilled in the art will adjust relief valve 43 to open in the pressure range of 500 to 600 millibar. The relief valve allows for the release of excess suction in the system, thereby preventing uncomfortable and potentially harmful pressure differences from occurring in the system. In the preferred embodiment, relief valve 43 is provided as a safety backup.

Figure 4A:
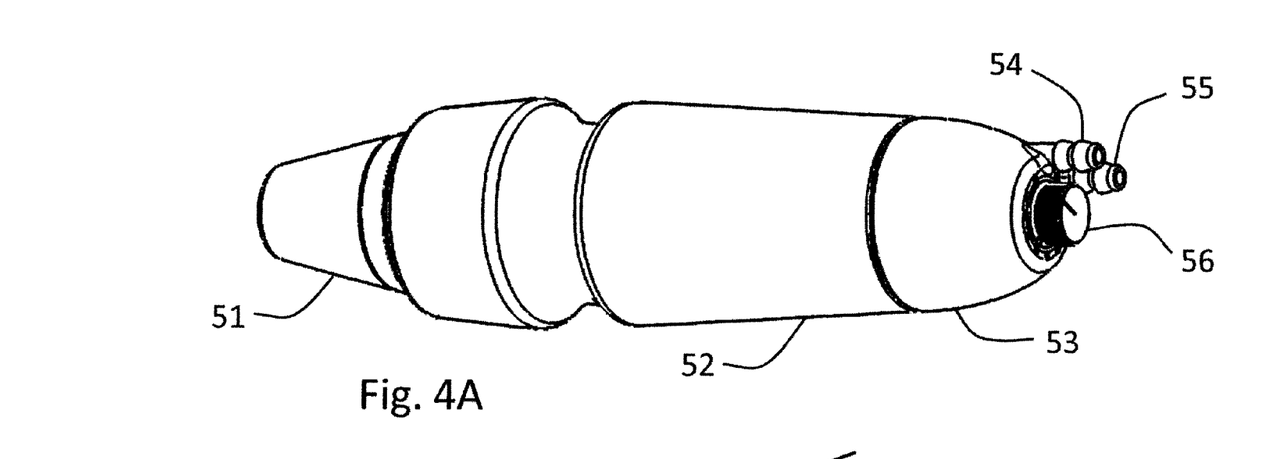
FIG. 4A illustrates an isometric external view of the hand piece of the present invention.
Figure 4B:
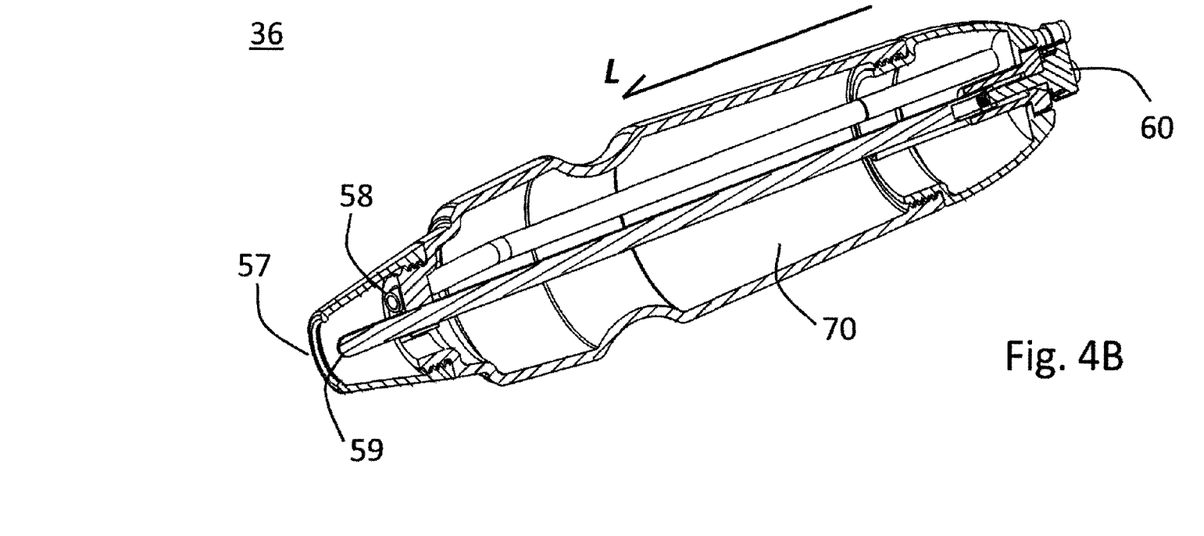
FIG. 4B illustrates an isometric cross-section view of the interior of the hand piece of the present invention.

FIG. 4A illustrates an isometric external view of the hand piece 36 and FIG. 4B illustrates an isometric cross-section view of the interior of the hand piece 36 of the present invention. Referring to FIG. 4A a hand piece assembly 36 is comprised of a proximal end 51, a main body 52, and a distal end

53. Together, these parts form a hollow cavity 70. Hand piece assembly 36 is adapted to be easily held in the hand, much like a pencil. Distal end 53 contains a supply port 54, an exhaust port 55, and an adjustment thumbscrew 56. Supply port 54 and exhaust port 55 are in fluid communication with the hand piece cavity 70. Referring now to FIG. 4B, proximal end 51 contains an operation orifice 57 and an abrasive supply jet 58. Abrasive supply jet 58 has a diameter of about 0.7 mm, and is a smaller diameter than either supply port 54 or exhaust port 55. Distal end 53 contains a vacuum relief valve assembly 60. Near the proximal end 51, vacuum relief valve assembly 60 has a proximity sensing skin probe tip 59. Operation orifice or treatment orifice 57 is a generally round hole or aperture that allows a seal to form with a mostly planar surface of skin. The edge of operation orifice 57 can be smooth or very rough. It is well known in the prior art to coat the edge of operation orifice with diamond particles to aid the abrasion effect of the flow-driven particles which impact the skin at the center of operation orifice 57. When operation orifice 57 is compressed against a flat skin surface, a seal is formed such that a vacuum applied at exhaust port 55 will cause an equal vacuum to form within the hand piece cavity 70 and at supply port 54. If supply port 54 is in fluid communication with an abrasive particle canister 34 and ambient air 75, a flow of abrasive particles 45 will travel through supply port 55, and out of supply jet 58. Supply jet 58 is located such that the momentum of the exiting abrasive particles causes the particles to impact the skin surface and become dispersed within the hand piece cavity 70. Thereafter the particles will be driven by the airflow to travel out of the hand piece cavity via exhaust port 55. In the preferred embodiment, supply jet 58 is placed at an angle to the planar skin surface. The angle depends on the distance of supply jet 58 from the skin surface, but is chosen so that the particles traveling out of supply jet 58 impact the skin surface at the center of operation orifice 57.

Hand piece parts, including proximal end 51, body 52, and distal end 53 are typically composed of polycarbonate, epoxy, stainless steel or titanium. Supply jet 58 and proximity sensing skin probe tip 59 must sustain exposure to high speed abrasive particles and are therefore typically manufactured from ceramic, glass, stainless steel or titanium. Supply port 54 and exhaust port 55 are exposed to slower particles and are usually composed of stainless steel, titanium, plastic, ceramic or glass. Flexible tubes a normally used to connect supply port 54 and exhaust port 55 with the remainder of the microdermabrasion system to allow flexible movement by the operator.

Figure 5:
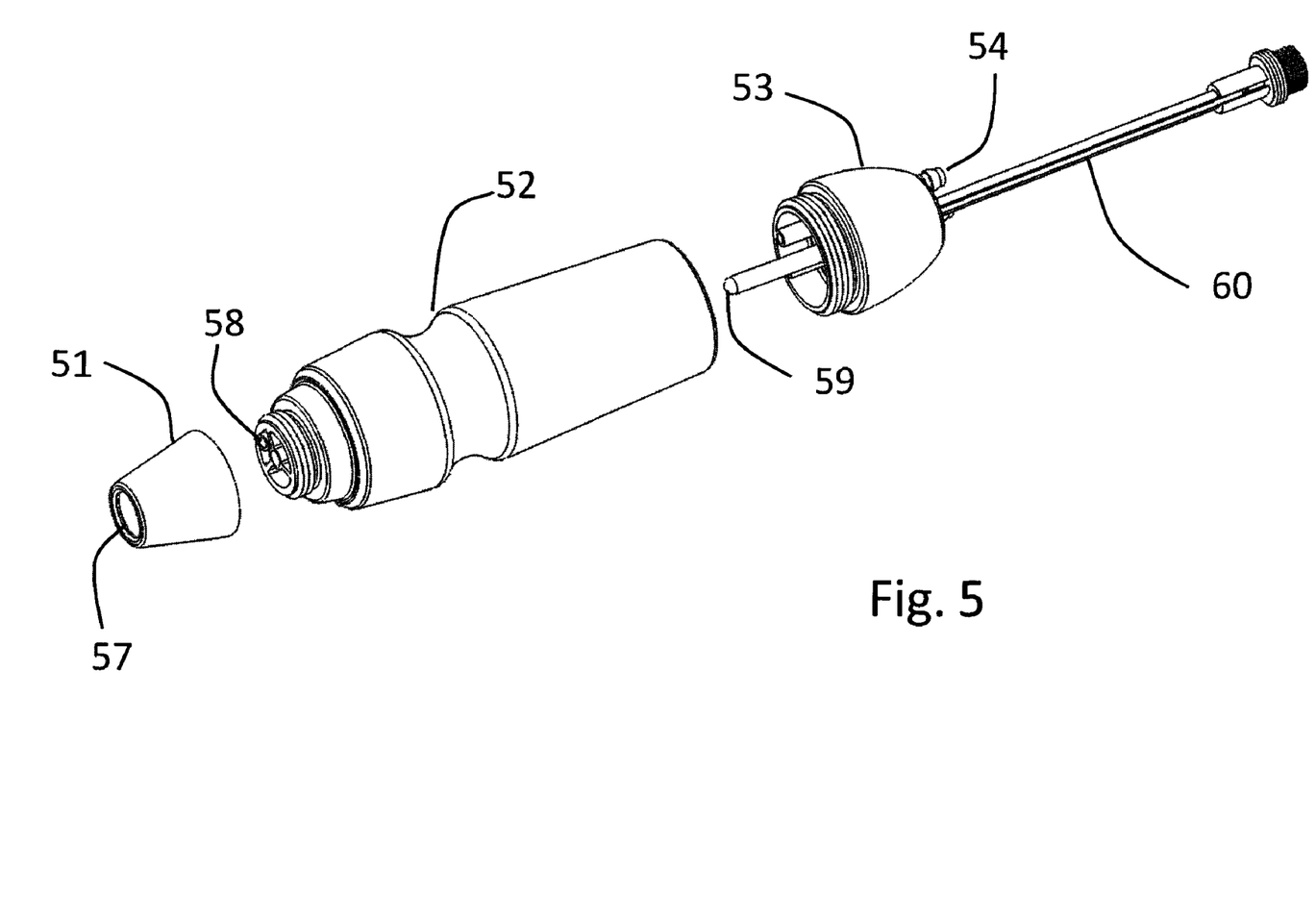
FIG. 5 illustrates an isometric exploded view of the major components of the hand piece.
Figure 6:
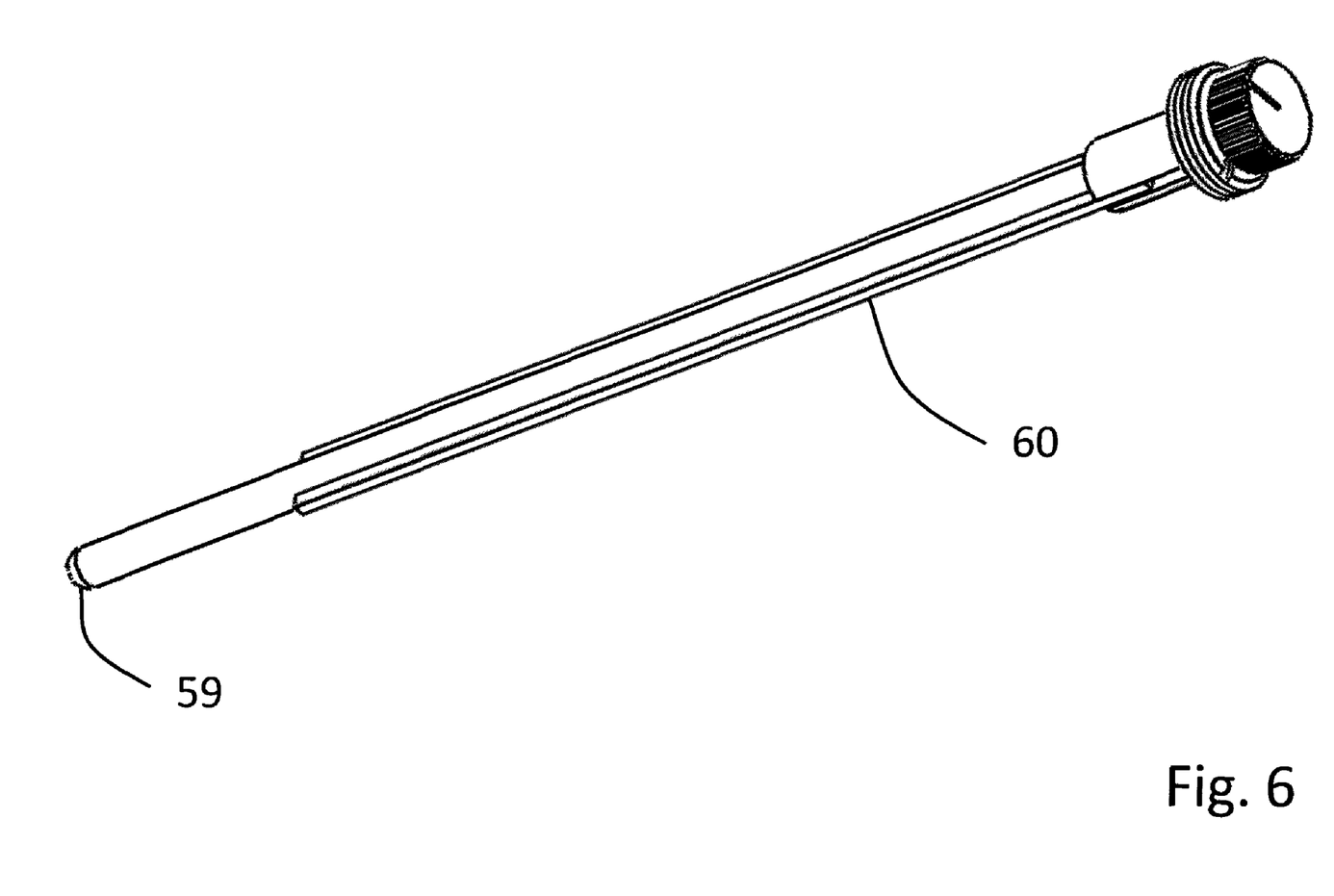
FIG. 6 illustrates an isometric view of the proximity sensing relief valve assembly.
Figure 7:
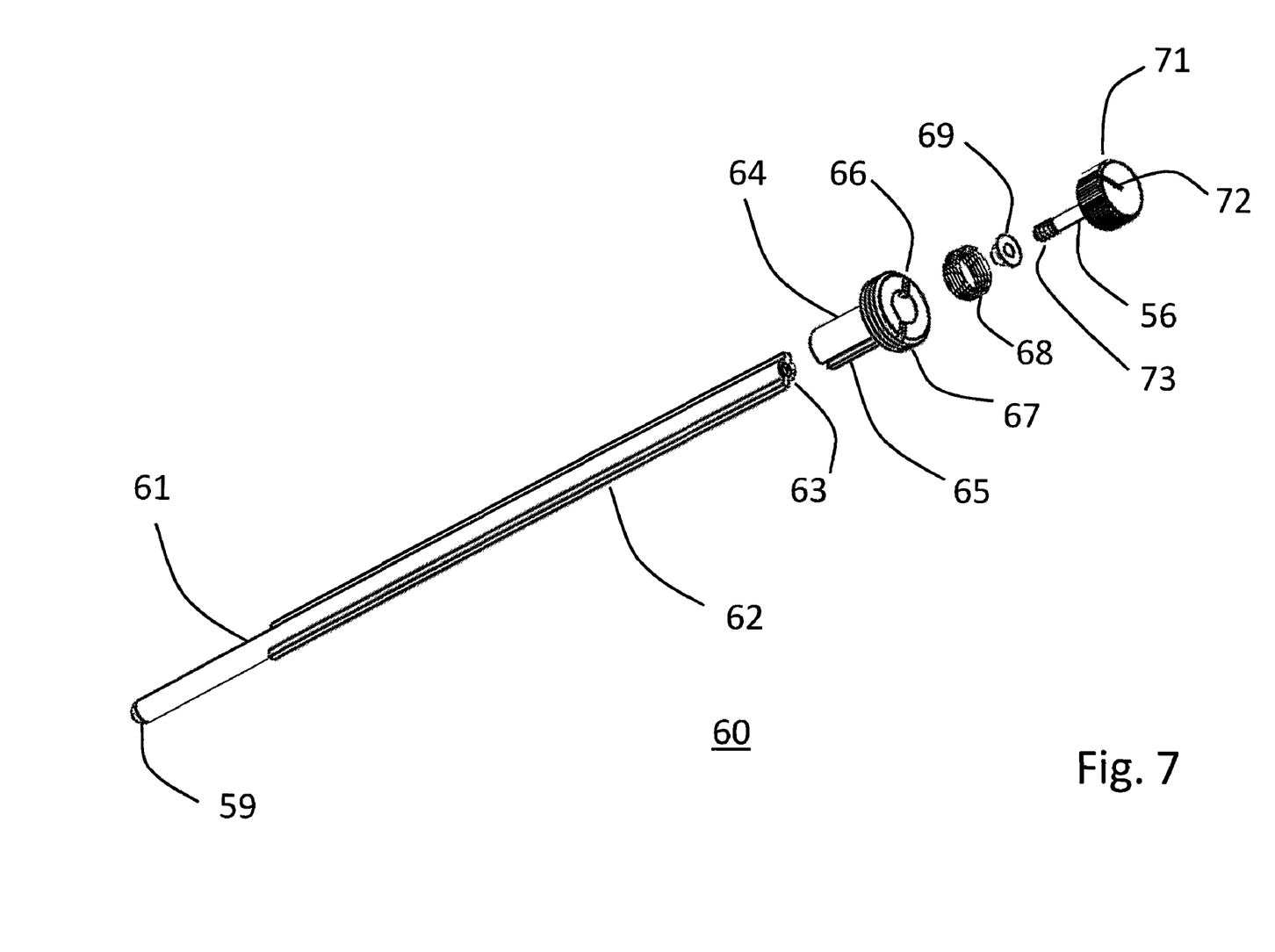
FIG. 7 illustrates an isometric exploded view of the major components of the proximity sensing relief valve assembly.

FIGS. 5-7 illustrate an isometric exploded view of the major components of hand piece assembly 36; an isometric view of proximity sensing relief valve assembly 60; and an isometric, exploded view of the major components of the hand piece 36 and the proximity-sensing vacuum relief valve assembly 60.

Skin probe shaft 61 contains proximity sensing skin probe tip 59 at the proximal end and female adjustment threads 63 at the distal end. Skin probe shaft 61 has non-rotation tabs 62 mounted along the length of the shaft. Proximity sensing relief valve 60 has a main body 64, which includes a number of non-rotation slots 65 designed to accept corresponding non-rotation tabs 62 of skin probe shaft 61. Main body 64 also has assembly slots 66 which enable main body 64 to be assembled into distal end 53 of hand piece assembly 36 by engagement of outer threads 67. Proximity sensing relief valve 60 has a compression spring 68, an elastomeric seal 69, and an adjustment thumbscrew 56. Adjustment thumbscrew 56 has a knurled edge 71 for a more secure adjustment, a rotation indicator line 72, and male adjustment threads 73, which engage the female threads 63 of skin probe shaft 61. Elastomeric seal 69 may be formed between 25-50 degrees, and is preferably formed at a 30-degree angle to the long axis of adjustment thumbscrew 56, with the smaller diameter end distal to the face of adjustment thumbscrew 56.

When proximity sensing relief valve 60 is threaded into hand piece assembly 36, main body 64 is stationary in relation to hand piece assembly 36. All other components of proximity sensing relief valve 60 are free to move axially, parallel to the long axis of hand piece assembly 36. Skin probe shaft 61 cannot rotate because non-rotation tabs 62 are captured by non-rotation slots 65 of main body 64. It can be seen that when adjustment thumbscrew 56 is rotated, skin probe shaft 61 will move axially, higher or lower, distally or proximally, along the long axis of hand piece assembly 36, and parallel to the longitudinal axis L.

Skin probe shaft 61 is in contact with high speed abrasive particles at skin probe tip 59 and the abrasive particle speed decreases as the distance from skin probe tip 59 increases. In the preferred embodiment skin probe shaft 61 is manufactured from ceramic, stainless steel or titanium. Compression spring 68 is preferably manufactured from a stainless steel. Spring rate or strength is selected to be strong enough to unseat the elastomeric seal in the absence of sufficient vacuum pressure, but weak enough to be overcome by the proper vacuum pressure inside the hand piece. Elastomeric seal 69 is preferably formed from a low durometer elastomer such as silicone having a durometer of about 50 Shore A. Adjustment thumbscrew 56 and main body 64 are typically manufactured from ceramic, stainless steel or titanium.

Figure 8A:
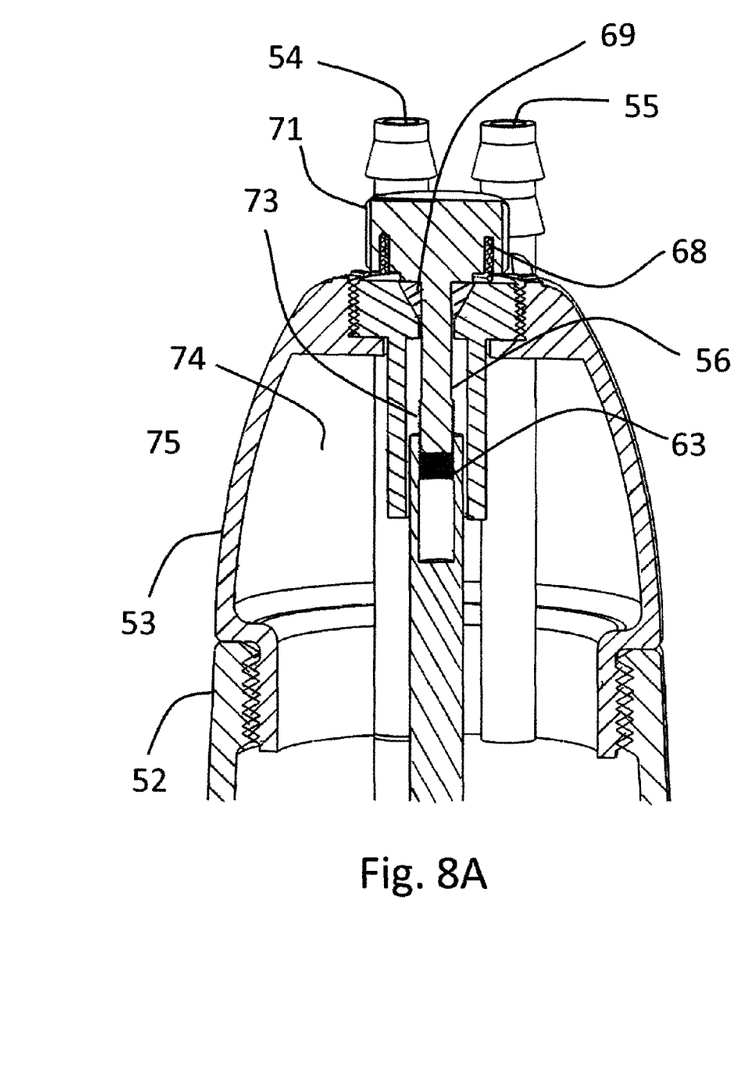
FIG. 8A illustrates a cross section view of the distal end of the hand piece showing that the proximity sensing relief valve is closed.
Figure 8B:
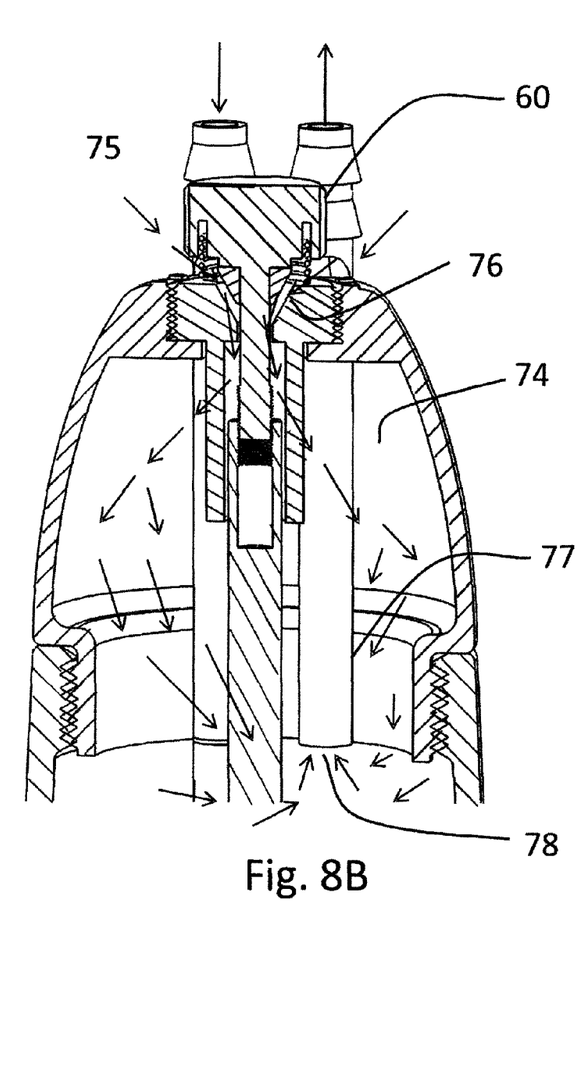
FIG. 8B illustrates a cross section view of the distal end of the hand piece showing that the proximity sensing relief valve is open.

FIG. 8A illustrates a cross section view of the distal end 53 of the hand piece 36 showing that proximity sensing relief valve 60 is closed. In operation, a vacuum in the hand piece cavity 74 provides a lower pressure in relation to the ambient pressure 75 which is external to hand piece assembly 36. Referring now to FIG. 8B, a cross section view of the distal end 53 of hand piece assembly 36 is illustrated with proximity sensing relief valve 60 in the open position.

Elastomeric seal 69 is separated from the sealing surface 76 of main body 64 in the absence of sufficient vacuum pressure inside the hand piece, or when the subject's skin contacts the skin probe. Sealing surface 76 matches the angle of elastomeric seal 69. An exhaust conduit 77 is shown oriented to the long axis of hand piece assembly 36. At the distal end of exhaust conduit 77 is exhaust port 55 and at the proximal end is exhaust conduit entrance port 78. Exhaust conduit 77 is exposed to high speed abrasive particles and is typically manufactured from ceramic, stainless steel, or titanium.

Figure 9A:
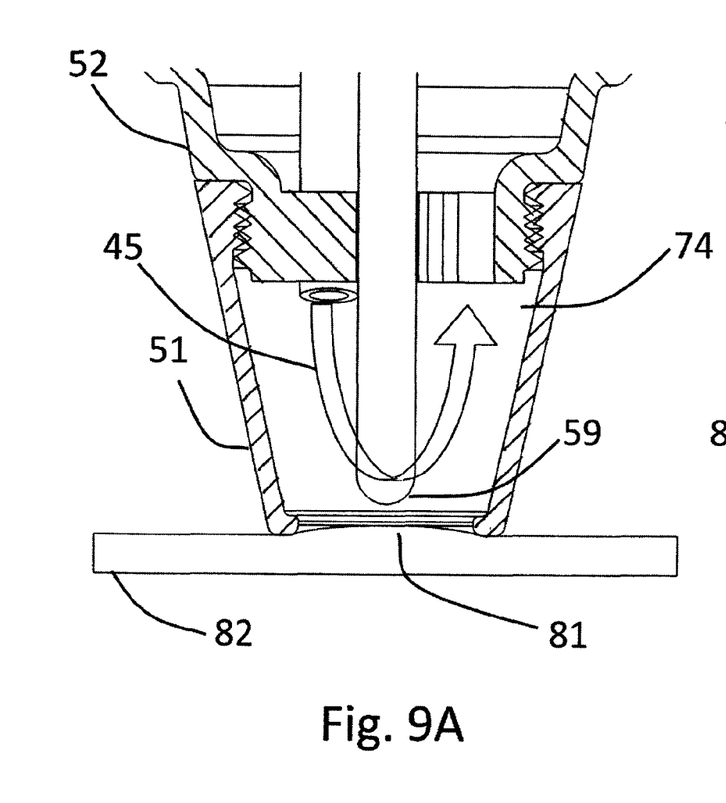
FIG. 9A illustrates a cross section view of the proximal end of the hand piece showing normal extension of the subject's skin.
Figure 9B:
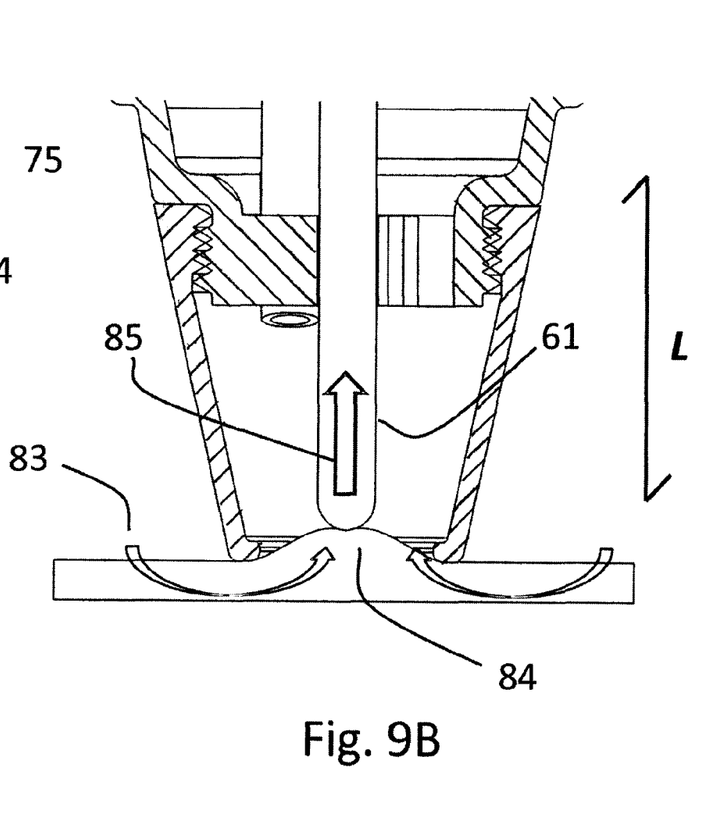
FIG. 9B illustrates a cross section view of the proximal end of the hand piece showing extension of the subject's skin that is limited by the proximity sensing relief valve.

FIG. 9A illustrates a cross section view of the proximal end 51 of hand piece assembly 36 showing a normal extension 81 of the subject's skin 14. FIG. 9B illustrates a cross section view of the proximal end 51 of hand piece assembly 36 showing extension 84 of subject's skin 14. During operation, pressure within cavity 74 is lower than that of ambient pressure 75. This pressure imbalance causes a force 83 to extend subject's skin 14 into hand piece cavity 74. Movement of operation orifice 57 over thinner areas of subject's skin 14 will cause hyperextension and trauma in the prior art. However, in the present invention, extension of subject's skin 14 into cavity 74, beyond an adjustable limit, causes contact with skin probe tip 59. This contact causes an upward motion 85 of skin probe shaft 61.

Referring back to FIG. 8B, upward motion of skin probe shaft 61 causes unseating of elastomeric seal 69. Referring again to FIG. 9B, said unseating allows a decrease in the pressure imbalance between cavity pressure 74 and ambient pressure 75. This decrease in the pressure imbalance causes force 83 to decrease, allowing normal skin extension 81 as shown in FIG. 9A. Loss of contact between skin probe tip 59 and subject's skin 82 allows reseating of elastomeric seal 69 onto sealing surface 69 as shown in FIG. 8A.

CONCLUSION, RAMIFICATIONS, AND SCOPE

Skin damage from microdermabrasion procedures is a function of time and vacuum level. Although the vacuum generator can produce 200 millibar (about 800 millibar below atmosphere) it takes time to build up to this level, as much as a minute depending on the particular equipment. The hand piece is, or should be, constantly moving, so there is an imperfect seal with the skin. Accordingly, the actual time in any one skin location is limited to a couple of seconds, and the normal vacuum may reach 800 millibar, which is 200 millibar below standard atmospheric pressure. At this vacuum level the prior art device will still have problems adapting to different skin thicknesses without damaging the skin.

A particular danger with prior art systems is when the hand piece is moved too slowly, and is too long in any skin location; and when the skin/treatment orifice sealing is too good, such as oiled skin. For example, only 30 seconds in a single location may allow the vacuum pressure to reach to 400 millibar (600 millibar below atmospheric pressure) which can produce huge blisters. The prior art system relies upon a relief valve located in the vacuum line between the vacuum generator and the hand piece, set at 500 to 600 millibar (400 to 500 millibar below atmospheric pressure), to prevent something catastrophic from happening. However, the prior art has no ability to be response to skin extension, regardless of vacuum pressure, such as the claimed invention. Of course, the present invention would certainly prevent such catastrophic events, no matter what the vacuum level, skin type, level of sealing, or length of time in one spot because operation is it is regulated by skin extension beyond a predetermined limit, not by transient vacuum level.

A hand piece used for microdermabrasion which automatically limits skin hyperextension is provided. The hand piece contains a longitudinally-oriented proximity vacuum relief valve which reduces trauma and bruising during a microdermabrasion procedure. Whereas higher vacuum levels and aggressive abrasion techniques are beneficial for promoting skin rejuvenation, the current invention allows a higher vacuum level and more aggressive abrasion technique on a variety of skin sites due to the limitation of skin hyperextension. The device produces superior results that are less dependent on operator skill.

The disclosed arrangement permits a user to select a predetermined limit for skin extension, based on the repeatably adjustable and variable length of the proximity-sensing skin probe tip relative to the treatment orifice and/or a predetermined and variable skin pressure required to activate the proximity-sensing vacuum relief valve assembly. Extension of the skin beyond this predetermined limit, which may be hyperextension, automatically triggers a vacuum release due to the longitudinal displacement of the skin probe shaft of the vacuum relief valve assembly.

We claim:
1. A microdermabrasion hand piece comprising:
an elongated body portion having a particle supply channel and a waste removal channel extending lengthwise, parallel to a longitudinal axis, through the body portion;
a removable tip attachable to a proximal end of the body portion, the removable tip defining a treatment orifice;
the particle supply channel being oriented to direct a stream of abrasive particles, which are drawn into and guided through the particle supply channel, substantially toward a center of the treatment orifice; and
an automatic vacuum relief valve assembly including an axially-movable skin probe oriented centrally in the hand piece and generally parallel to the longitudinal axis of the hand piece, the axially-movable skin probe being movable in response to skin contact,
wherein the hand piece provides automatic limitation on skin extension, wherein extension of the skin in the treatment orifice beyond a predetermined limit is prevented and excessive extension of skin of various thicknesses is eliminated.

2. The microdermabrasion hand piece of claim 1, an abrasive supply jet is radially displaced from the longitudinal axis of the hand piece, wherein the stream of abrasive particles exits the particle supply channel at a point which is radially displaced from the vacuum relief valve assembly on the longitudinal axis of the hand piece.

3. The microdermabrasion hand piece of claim 1, wherein the particle supply channel is angularly offset relative to the longitudinal axis of the hand piece, wherein delivery of the stream of abrasive particles is not parallel to the longitudinal axis.

4. The microdermabrasion hand piece of claim 1, wherein the diameter of the waste removal channel inside the proximal end of the hand piece is larger than the diameter of the particle supply channel.

5. The microdermabrasion hand piece of claim 4, wherein the diameter of the waste removal channel inside the proximal end of the hand piece is 1.5 to 3 times larger than the diameter of the particle supply channel.

6. The microdermabrasion hand piece of claim 1, wherein the treatment orifice is generally perpendicular to the longitudinal axis of the hand piece.

7. The microdermabrasion hand piece of claim 1, wherein the treatment orifice is angled with respect to the longitudinal axis of the hand piece.

8. The microdermabrasion hand piece of claim 1, wherein the axially-movable skin probe is movably attached to the distal end of the hand piece and being movable in response to skin contact.

9. The microdermabrasion hand piece of claim 1, wherein axial displacement of the axially-movable skin probe opens a valve to admit ambient air and reduce the vacuum pressure inside the hand piece.

10. The microdermabrasion hand piece of claim 1, wherein the vacuum relief valve assembly is user-adjustable for a maximum skin extension to be achieved before automatic actuation of the vacuum relief valve occurs.

11. The microdermabrasion hand piece of claim 8, wherein the axially-movable skin probe includes one or more non-rotation tabs oriented longitudinally along the skin probe and projecting radially from the skin probe, said non-rotation tabs engaging one or more corresponding slots in a generally tubular main body of the vacuum relief valve assembly, said generally tubular main body being attached to the distal end of the hand piece body.

12. The microdermabrasion hand piece of claim 11, wherein the vacuum relief valve assembly further comprises an adjustment thumbscrew having a manually-manipulated head and a threaded shaft extending longitudinally therefrom, the threaded shaft having male threading and extending through the generally tubular main body, wherein the male threading engages female threading of the distal end of the axially-movable skin probe, wherein rotation of the adjustment thumbscrew adjusts the axial position of the skin probe with respect to the treatment orifice, and adjusts the sensitivity of the axially-movable skin probe to skin contact.

13. The microdermabrasion hand piece of claim 12, wherein the one or more slots in the generally tubular main body are limited to the proximal end of the generally tubular main body, such that the axially-movable skin probe cannot move axially entirely through the main body, and further comprising a coil spring between the adjustment thumbscrew and the generally tubular main body, wherein the adjustment thumbscrew and the axially-movable skin probe are biased distally away from the proximal end of the hand piece, wherein vacuum pressure within the hand piece overcomes the biasing force of the spring and draws the adjustment thumbscrew and axially-movable skin probe toward the proximal end of the hand piece, wherein rotation of the adjustment thumbscrew adjusts the sensitivity of the axially-movable skin probe to skin contact in a predictable manner.

14. The microdermabrasion hand piece of claim 13, further comprising an elastomeric seal around the shaft of the adjustment thumbscrew immediately adjacent the manually-manipulated head, wherein the elastomeric seal bears against a corresponding sealing surface in the distal end of the main body to provide a positive and releasable vacuum seal, wherein axial movement of the skin probe, in response to skin contact, unseats the elastomeric seal and reduces the vacuum pressure within the hand piece and treatment orifice.

15. The microdermabrasion hand piece of claim 14, further comprising a rotation indicator on the manually-manipulated head of the adjustment thumbscrew, providing visual confirmation of a relative sensitivity of the hand piece.

* * * * *